United States Patent [19]

Hubbs et al.

[11] Patent Number: 5,192,542
[45] Date of Patent: Mar. 9, 1993

[54] TISSUE SEALANT PRODUCT AND METHOD

[76] Inventors: James J. Hubbs, 1939 E. Apollo, Tempe, Ariz. 85254; Jonathan Hubbs, 3131 E. Mulberry, Phoenix, Ariz. 85016

[21] Appl. No.: 473,927

[22] Filed: Feb. 2, 1990

[51] Int. Cl.$^5$ .................. A61K 35/78; A01N 1/00
[52] U.S. Cl. .................. 424/195.1; 424/75; 514/783
[58] Field of Search .............. 424/195.1, 75; 514/783

[56] References Cited

U.S. PATENT DOCUMENTS 4,827,665  5/1989  Hubbs, Jr. et al. .................. 47/58

FOREIGN PATENT DOCUMENTS 662509  5/1963  Canada .

OTHER PUBLICATIONS

"Healing, antiseptic and antiinflammatory product for external use", Rizescu et al. CA 99 (10): 76909t.
"Physiologically active alcohols of Plantago Major" Mironor et al., CA 100(5):32223Z.
"The Herb Book", John B. Lust, First Edition pp. 304-306.

*Primary Examiner*—Johnnie R. Brown
*Assistant Examiner*—Ralph G. Gitomer
*Attorney, Agent, or Firm*—Gregory J. Nelson

[57] ABSTRACT

A product and method of treating tissue particularly during the embalming process. The product is produced by drying and finely grinding plants from the Plantain family to a powder. The method involves applying the powder to wounds, incisions and the like to form closure.

3 Claims, No Drawings

TISSUE SEALANT PRODUCT AND METHOD

The present invention relates to a tissue sealant method and more particularly relates to a method for sealing bodily tissue during embalming procedures.

In embalming procedures, bodily wounds, incisions, excisions, sutures, needle holes and the like are often sealed for cosmetic reasons. The procedure usually involves applying a sealant and preservative composition which will contact and seal the wound. The purpose of such a seal is to form a closure which is cosmetically acceptable and which will bond with the tissue to reduce weeping and seepage from these wounds and to suppress offensive odors.

In conventional practice several compositions, mainly organic in nature are available for this purpose. One particular composition is sold under the name "Dodge Q-S Quick Sealing Powder". Compositions such as the sealant mentioned above are effective but do have certain disadvantages in some applications. Conventional sealing compositions do not always quickly bond and conform to the tissue. Further, conventional sealants for this purpose will also cause localized dehydration which degrades the desired cosmetic effect.

Accordingly, there exists a need for an effective tissue sealant for medical and embalming applications which is absorbent and will quickly bond to tissue areas.

Accordingly, it is the primary object of the present invention to provide a tissue sealant and preservative which will adhere to incisions, wounds, lesions, sutures and needle holes and the like to form a seal to prevent leakage and to neutralize offensive odors.

Another object of the present invention is to provide a natural sealant having characteristics that will absorb and bond to tissue.

It is another object to provide a tissue sealant derived from plants of the Plantain family which quickly forms an elastic, absorbent layer when applied to tissue.

Briefly, the present invention provides an improved tissue sealant and method of treating tissue. The sealant is a natural product derived from the dried and ground plants from the Plantain family. The tissue treatment procedure involves applying the finely ground seed and part of the plant from the Plantain family to the tissue to form a seal conforming the tissue with no visible tissue distortion to prevent leakage and to suppress odors.

In the practice of the present invention, the sealing powder is first prepared. The sealant is prepared by harvesting herbs from the Plantain family (Plantaginaceae). The genus of the Plantain family is described as Plantago. The plant is described as a generally scapose, herb with foliage leaves all basal; flowers small, perfect or unisexual, regular, in interminal, long-pedunclaed, bracted spikes; calyx and corolla 4-divided or 4-lobed, persistent, usually scarious or scariuos-margined; stamens 2 or 4, distinct, attached to the corolla tube; style filiform, stigmatic most of its length; ovary superior, 2 to 4 celled; fruit a circumscissile, usually few-seeded capsule. See Arizona Flora, by Kearny and Peebles (1951 with Supplement 1960).

There are various species to the Plantain family and such species as Plantago Insularis, Plantago Lanzeolata and Plantago Major, found in Utah, Nevada, Arizona and southern California, and have been found to be particularly well-suited for this purpose. The Spanish Psyllium, not native to America, may also be suitable for this purpose. In the preparation of the sealant, the plant is initially harvested by cutting it mid-stem and then drying. Drying can be accomplished naturally on drying racks or tables exposed to solar energy or can be accomplished in conventional agricultural driers. After the plant has dried, it is ground to a fine powder. Grinding can be accomplished by any number of conventional techniques including use of ball grinders, augers or screening techniques. Preferably the dried plant is ground to approximately the consistency of ordinary talcum powder which is about mesh 150-200. Some inert fillers may be added if bulk is required. Typical fillers may be organic ground material such as seed husk, leaves and stems. The sealant is now ready for application.

It is noted that the material described herein as a tissue sealant has previously been described in U.S. Pat. No. 4,827,665 as a product for conditioning soils and also utilized in connection with the method of treating soil for better water dispersion and retention.

In the embalming process, various tissue openings such as surgical incisions, excisions, amputations, wounds, sutured needle holes, eye enucleations, and autopsies generally requiring sealing. In accordance with the method of the present invention, the finely milled sealant prepared as described above can be directly applied to the area to be treated. The natural properties of the sealant absorb moisture and quickly form a bond with tissue. It has been found that the sealant will continue to absorb up to about seventy-five times its own weight, generally forming an elastic membrane-type seal which is impermeable to moisture. Thus, the sealant will prevent leakage and escape of odors from the treated area are minimized and controlled.

It has been found that the sealing action is quick and that the sealant will bond quickly to moist areas and conform to tissue with no visible distortion.

The application of the sealant to the wound may be directly from the container, thus the sealant is quick and easily applied. The sealant may also be applied with various conventional applicators for specialized treatment.

In some situations where a large cavity is to be filled or treated, the composition also may be mixed with conventional embalming fluids which typically contain aldehydes, alcohols, phenols, glycerine and similar chemicals and applied in this manner to the cavity to form a filler and sealant.

One particular advantage of the sealant of the present invention is that it seals without dehydrating the adjacent tissue area. As mentioned above, many conventional sealants for this purpose will dehydrate the area which causes a discoloration of the tissue which is cosmetically unacceptable.

The sealant of the present invention is derived from the plant of the Plantago family and accordingly is a natural, organic product. It does not easily disperse into the air when applied or dispensed and accordingly may be used safely by the embalmer. However, good practice suggests that precautions against inhalation should always be taken.

While the Plantago species, Plantago Lanzeolata, Plantago Major and Plantago Insularis, are particularly suitable for producing a tissue sealant, other species within in the family may be used. They include Plantago ovata, Plantago purshii and Plantago fastigiata.

Having described in detail the preferred embodiment of my method for tissue treatment, a person skilled in the art will be able to take the teachings hereof and make various changes, alterations and modifications while continuing to practice the inventive principals described herein. It is therefore intended all such modifications and alterations be covered as they are embraced within the spirit and scope of the appended claims.

I claim:

1. A method of treating tissue of a corpse in an embalming procedure comprising applying a sealant to the area to be treated consisting of the dried and ground plants selected from the group consisting of: Plantago Insularis; Plantago Lanceolata; Plantago Ovata; Plantago Fastigium; and Spanish Psyllium to form a seal in the area bonded to tissue to minimize fluid leakage and escape of odor.

2. The method of claim 1 in which said sealant is ground to a mesh of approximately 150 to 200.

3. The method of claim 2 wherein said sealant is mixed with an embalming fluid and applied to the tissue area.

* * * * *